United States Patent [19]
Lester et al.

[11] Patent Number: 5,169,401
[45] Date of Patent: Dec. 8, 1992

[54] SURGICAL REAMER ASSEMBLY

[75] Inventors: Mark B. Lester; Milton F. Barnes, both of Warsaw, Ind.

[73] Assignee: Zimmer, Inc., Warsaw, Ind.

[21] Appl. No.: 811,101

[22] Filed: Dec. 20, 1991

[51] Int. Cl.⁵ .................... A61B 17/00; A61F 2/32
[52] U.S. Cl. .............................. 606/79; 606/80; 606/99; 623/23
[58] Field of Search .......... 606/79, 80, 60, 62, 606/65, 67, 69, 71, 72, 85, 86, 87, 88, 89, 90, 96, 99; 623/22, 23, 21

[56] References Cited

U.S. PATENT DOCUMENTS

| | | | |
|---|---|---|---|
| 2,785,673 | 3/1957 | Anderson | 128/92 |
| 3,874,003 | 4/1975 | Moser et al. | 3/1 |
| 3,894,297 | 7/1975 | Mittelmeier | 623/22 |
| 4,004,581 | 1/1977 | Heimke et al. | 128/92 E |
| 4,187,559 | 2/1980 | Grell et al. | 3/1.91 |
| 4,306,550 | 12/1981 | Forte | 128/92 E |
| 4,467,801 | 8/1984 | Whiteside | 128/303 R |
| 4,535,487 | 8/1985 | Esper | 623/22 |
| 4,601,289 | 7/1986 | Chiarizzio | 623/23 |
| 4,659,067 | 4/1987 | Fournier | 623/23 |
| 4,661,112 | 4/1987 | Müller | 623/22 |
| 4,765,328 | 8/1988 | Keller | 623/23 |
| 4,790,852 | 12/1988 | Noiles | 623/23 |
| 4,921,493 | 5/1990 | Webb, Jr. et al. | 606/85 |
| 4,944,762 | 7/1990 | Link et al. | 623/23 |
| 4,963,155 | 10/1990 | Lazzeri | 623/23 |
| 4,998,937 | 3/1991 | Grimes | 606/89 |
| 5,002,578 | 3/1991 | Luman | 623/23 |
| 5,002,581 | 3/1991 | Paxson | 623/23 |
| 5,019,108 | 5/1991 | Bertin | 623/23 |

OTHER PUBLICATIONS

Waldemar Link literature—Link Calcar Reamer—1983.
Zimmer, Inc. literature—Surgical Technique, Harris/Galante Porous Hip Prothesis—Lit. No. 85-037-90-26-0348, Rev. 2—p. 23—1984.
Zimmer, Inc. literature—The Total System—Lit. No. 85-037-9026-0326, Rev. 2—pp. 20-21—1984.
Zimmer, Inc. literature—BIAS Total Hip System, Surgical Technique For Cementless Primary Hip Arthroplasty—Lit. No. 97-6550-09—1989.
Zimmer, Inc. catalog p. A42—Prod. No. 6551-07, BIAS Hip Calcar Rasp—1987.
Zimmer, Inc. literature—Modular Austin Moore Hip—Lit. No. 97-4555-01—1990.
Zimmer, Inc. literature—Anatomic Hip Prosthesis—Lit. No. 97-6600-01—1990.

*Primary Examiner*—Michael A. Brown
*Attorney, Agent, or Firm*—Margaret L. Geringer

[57] ABSTRACT

A surgical reamer assembly for cutting a planar bone surface. The surgical reamer assembly enables the angle or the level of the cutting of the planar reamer to be adjusted. This adjustment is advantageously provided by the use of an adaptor which is positioned between the base support and the planar reamer.

26 Claims, 4 Drawing Sheets

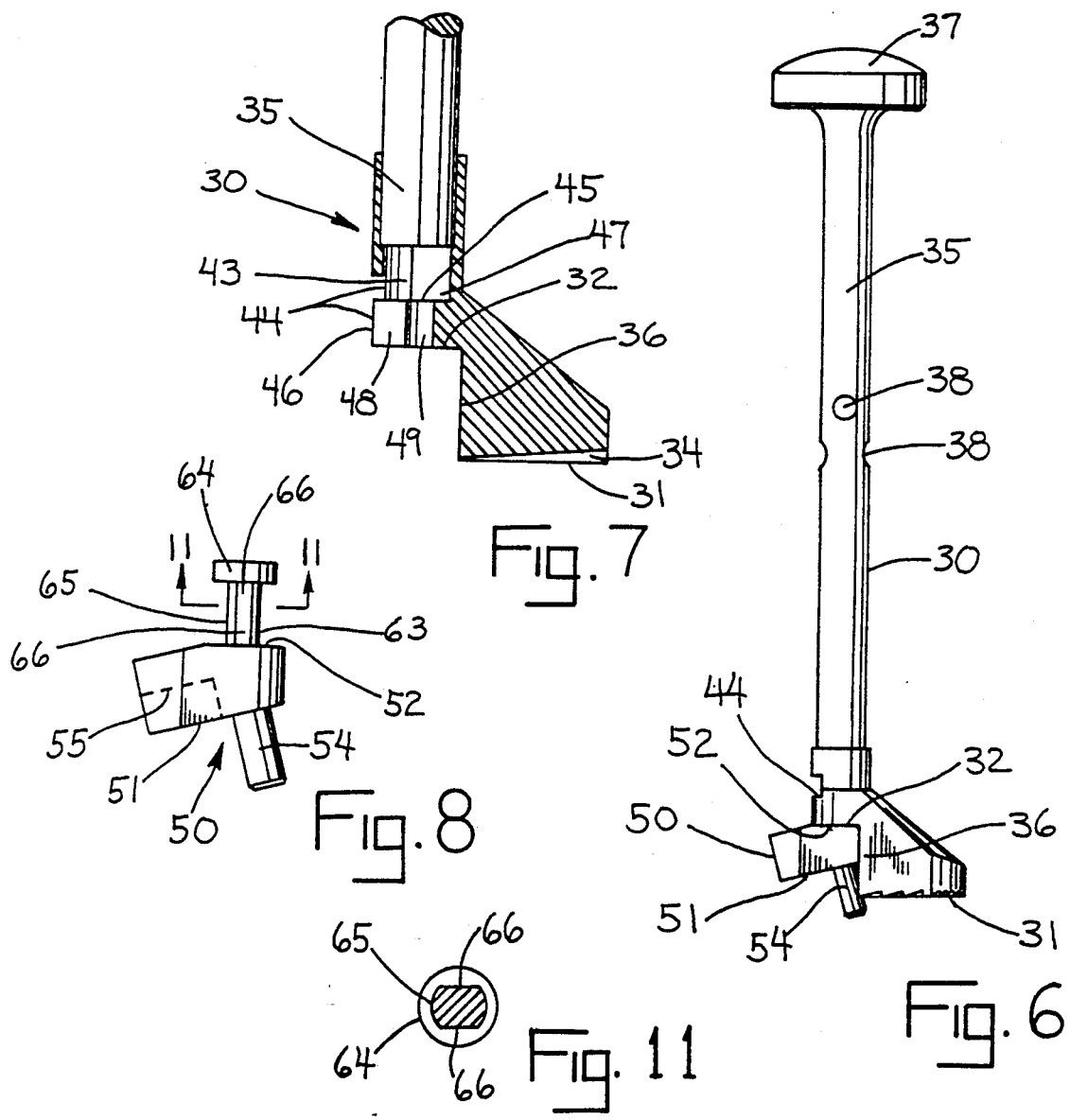

SURGICAL REAMER ASSEMBLY

The present invention relates to a surgical reamer assembly. specifically, the reamer assembly is used for cutting a planar bone surface.

The use of planar reamers for reaming or cutting a flat, planar surface on bone is well known in the orthopaedic industry. One such type of planar reamer is used for reaming the calcar bone of a femur to match the undersurface of an extending collar on a collared femoral hip prosthesis. Such a planar reamer is shown in FIG. 7 of U.S. Pat. No. 5,019,108 to Bertin et al. which shows a calcar reamer 40 with a pin 41 protruding from cutting surface 43. The pin 41 fits directly into hole 35 of rasp 30 (of FIG. 6) functioning as a pivot. Thus, pivoting the surface 43 about pin 41 planes the femoral bone to provide a flat bone contact to mate with the flat undersurface 18 of collar 17 of the hip implant 10.

Another such planar reamer is disclosed in U.S. Pat. No. 4,998,937 to Grimes. FIG. 9 shows a planar reamer 97 which fits directly over protruding pin 93 to ream a flat surface on the bone. FIG. 10 shows an alternate planing tool 99 with an integral post 103 depending therefrom which is inserted in an opening in barrel 15 to cut a planar surface.

In the above references, the planar reaming surface either has a pivot post protruding directly therefrom for fitting in a hole on a supporting surface or the planar reaming surface has a hole therein for fitting directly over a protruding post.

OBJECTS OF THE INVENTION

It is an object of the invention to provide a surgical reamer assembly for cutting a planar bone surface in which the angle or level of the cutting of the planar reamer is to be adjusted.

It is a further object of the present invention to provide a surgical reamer assembly which cuts a planar surface at a level that is below the level of the mating pivoting surfaces.

It is a still further object of the invention to provide an adaptor for positioning between the base support and the planar reamer.

It is another object of the invention to provide such an adaptor which enables reaming a planar surface at an angle different from the angle of the proximal planar surface of the base support.

SUMMARY OF THE INVENTION

The present invention provides a reamer assembly for cutting a planar bone surface. The surgical reamer assembly enables the angle or the level of the cutting of the planar reamer to be adjusted. This adjustment is advantageously provided by the use of an adaptor which is positioned between the base support on the planar reamer instrument.

BRIEF DESCRIPTION OF THE DRAWINGS

These features and objects of the invention, as well as others, will become apparent to those skilled in the art by referring to the accompanying drawings:

FIG. 3 is bottom plan view with a partial cross-section, of the adaptor of FIG. 2;

FIG. 4 is a rear elevation view of the adaptor of FIG. 2;

FIG. 5 is a bottom plan view of the planar reamer of FIG. 2

FIG. 6 is a side elevational view of an alternate embodiment for the adaptor and planar reamer of the present invention;

FIG. 7 is a partial cross-sectional view of the planar reamer of FIG. 6 with the cross-section taken along lines 7—7 of FIG. 10;

FIG. 8 is a side elevational view of the adaptor of FIG. 6;

FIG. 11 is a cross-sectional view of the post portion of the pivot pin of adaptor 50, with the cross-section taken along lines 11—11 of FIG. 8.

DETAILED DESCRIPTION OF THE INVENTION

FIGS. 1-5 illustrate a particularly advantageous embodiment of the surgical reamer assembly of the present invention, while FIGS. 6-11 illustrate an alternate advantageous embodiment of the invention. The invention will be described with reference to a surgical reamer assembly for planing a flat bone surface for mating with the flat undersurface of an extending collar on a collared femoral hip prosthesis. However, it is understood that the principles of the invention are applicable to a surgical reamer assembly for planing any suitable flat bone surface.

The embodiment of FIGS. 1-5 illustrate surgical reamer assembly 1. The assembly 1 includes a base support 10, a planar reamer 30, and an adaptor 50 for positioning between support 10 and reamer 30.

Figure 1:
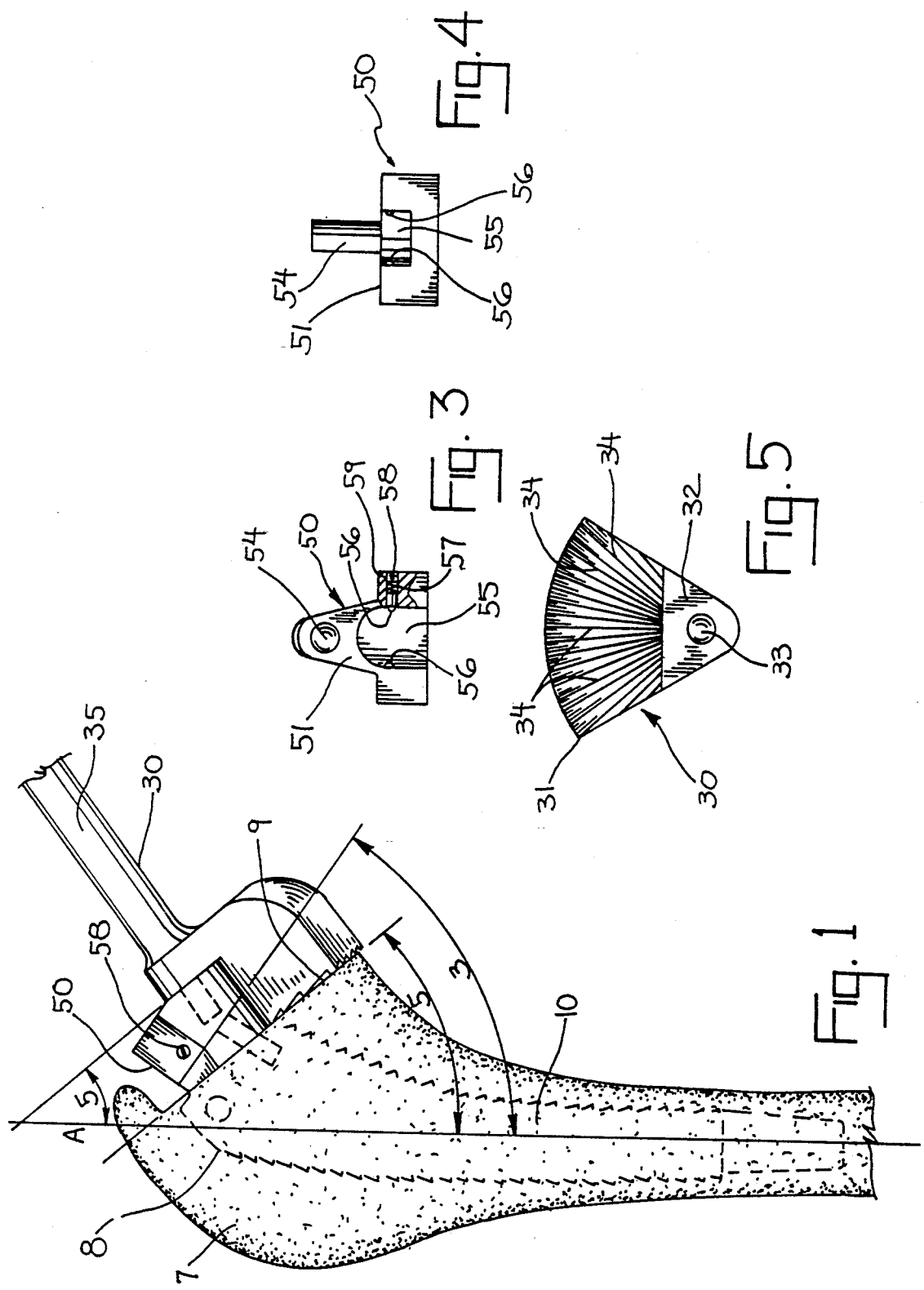
FIG. 1 is a side elevational view illustrating the surgical reamer assembly of the present invention shown in use on a femur.
Figure 2:
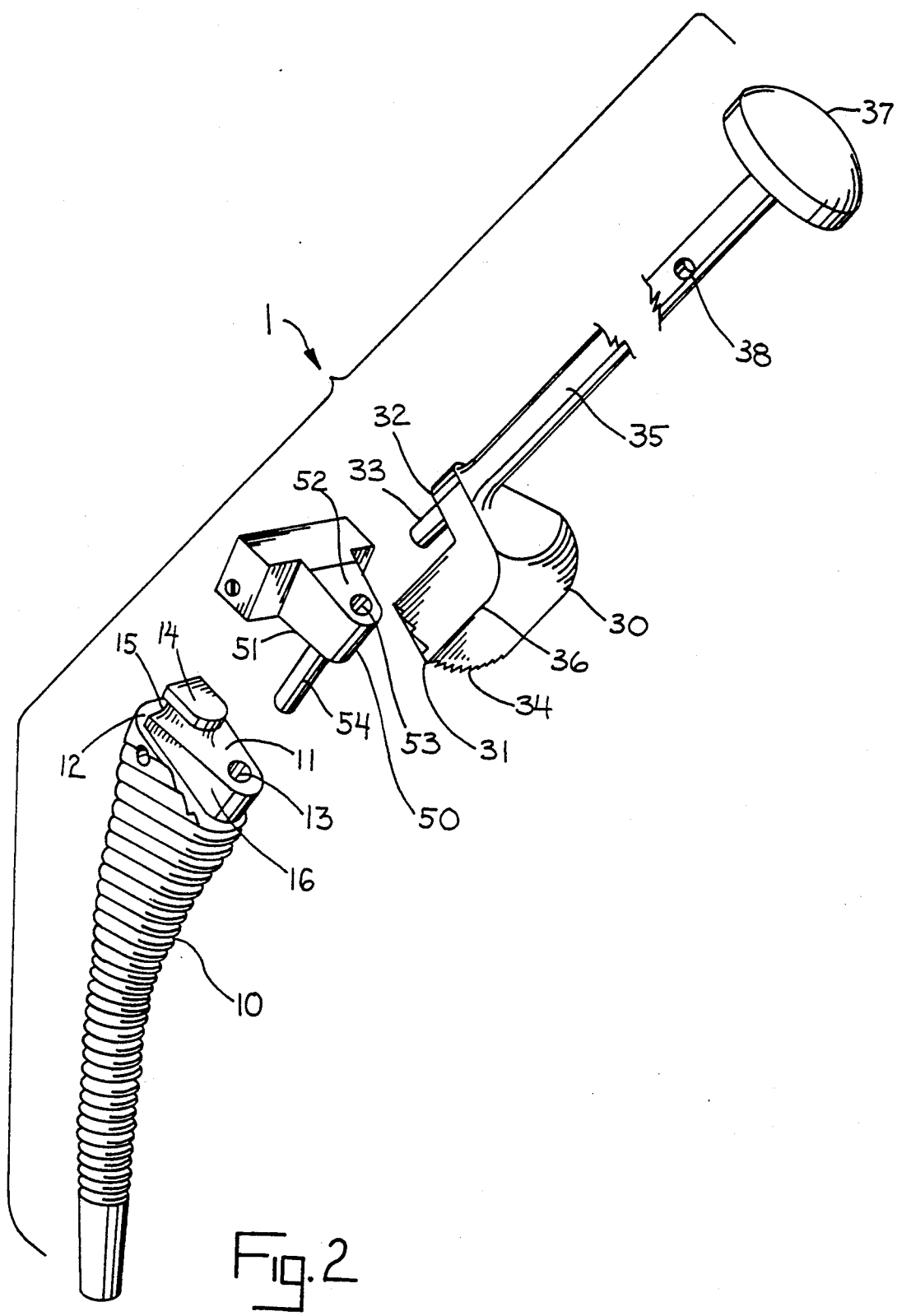
FIG. 2 is an exploded perspective view of the surgical reamer assembly of FIG. 1 including the base support, the adaptor, and the planar reamer.

The base support 10, as shown, may be a rasp cutter for forming a cavity 8 in the femoral bone 7, as shown in FIG. 1. The base support 10 in FIG. 1 is shown positioned in the femur 7. It is desired to cut or ream the femoral bone 7 to provide a flat planar bone surface 9 for mating with the flat undersurface of a collar on a corresponding collared femoral hip prosthesis (not shown).

The base support 10 has a proximal planar surface 11 which is oriented at a first angle 3 to reference axis A. Reference axis A, as shown, may suitably be the main axis of the elongated base support 10. The first angle 3 of proximal planar surface 11 may be designed and oriented to mate with other mating instrumentation (not shown), such as a releasable rasp handle and/or a cone or neck provisional for use during the surgical procedure. U.S. Pat. No. 4,921,493 to Webb, Jr. et al. shows an example of a releasable rasp handle, while U.S. Pat. No. 4,963,155 to Lazzeri et al. shows an example of cone or neck provisional, with a rasp cutter. Both of these patents are incorporated herein by reference.

The planar reamer 30 has a cutting surface 31 oriented at a second angle 5 to reference axis A. Cutting surface 31 will be used to cut corresponding flat planar bone surface 9 which will then be parallel to cutting surface 31. The second angle 5 is different from the first angle 3. The first angle may suitably be about 60 degrees to the reference axis, while the second angle may suitably be about 45 degrees to the reference axis. The planar reamer 30 also has a supporting planar surface 32 also oriented at second angle 5.

The adaptor 50 has a distal adaptor surface 51 oriented at first angle 3 for mating with and connecting to the proximal planar surface 11 of base support 10. The adaptor 50 also includes a proximal adaptor surface 52 oriented at second angle 5 for mating with the supporting planar surface 32 of planar reamer 30. The proximal adaptor surface 52 and the mating supporting planar surface 32 include a pivot mechanism therebetween to allow pivoting of the planar reamer 30 about the pivot mechanism to provide planar reaming with cutting surface 31.

The pivot mechanism includes a pivot pin 33 extending substantially perpendicularly from the supporting planar surface 32 of planar reamer 30, and the proximal adaptor surface 52 includes a pivot recess 53 for accepting the pivot pin 33 of planar reamer 30.

The planar reamer 30 includes an elongated handle 35 extending therefrom. Handle 35 may include an enlarged proximal knob 37 thereon. In addition, through holes 38 may be provided in handle 35 to accept a cross rod (not shown) therethrough. Such cross rods are known for use with planar reamers.

The cutting surface 31 depends from the supporting planar surface 32, and is connected to the supporting planar surface 32 by a connecting portion 36, such that the cutting surface 31 is parallel to, but non-coplanar with the supporting planar surface 32. The cutting surface 31 is lower than the proximal planar surface 11 of base support 10 when the reamer 30, adaptor 50 and base support 10 are assembled together. The connecting portion 36 is laterally spaced from pivot pin 33 to provide sufficient clearance for pivoting about adaptor 50 and base support 10. The cutting surface 31 of planar reamer 30 includes cutting teeth 34 thereon.

The base support 10 includes an extending ledge surface 12 about the base support 10 which is spaced below the proximal planar surface 11. The ledge surface 12 is separated from the proximal planar surface 11 by a raised wall 16. The ledge surface 12 is oriented at second angle 5. The cutting surface 31 of planar reamer 30 is substantially coplanar with ledge surface 12 when the base support 10, adaptor 50, and planar reamer 30 are assembled together, as shown in FIG. 1, to provide planar cutting via cutting surface 31 oriented at the second angle 5.

The adaptor 50 and the base support 10 are releasably assembled together, so that the adaptor 50 does not rotate relative to the base support 10. The proximal planar surface 11 of base support 10 includes a locating recess 13 for accepting the corresponding locating pin 54 which extends from the distal adaptor surface. In order to prevent rotation of the locating pin 54 in locating recess 13, a raised spline 14 may be provided which extends from proximal planar surface 11. The spline 14 is spaced from locating recess 13. Accordingly, the distal adaptor surface 51 includes a corresponding spline receptacle 55 for receiving spline 14 of base support 10. The spaced interconnections of pin 54 with recess 13 and of spline 14 with spline receptacle 55 prevents rotation between the adaptor 50 and base support 10.

In order to releasably secure the adaptor 50 on base support 10, the spline 14 may be provided with a groove 15 for accepting biased ball plungers 56. Two oppositely located ball plungers 56 may be provided as shown in FIG. 3. The ball plungers 56 are biased to extend from adaptor 50 into spline receptacle 55, and thus into groove 15 of spline 14 when adaptor 50 is assembled to base support 10 to releasably retain adaptor 50 on base support 10. The biased ball plungers 56 are each biased by a connecting spring 57, such that the ball plungers 56 compress and recede into the adaptor as the ball plungers 56 pass over spline 14 upon the application of connection force to connect the adaptor 50 to base support 10 or upon application of separation force to remove adaptor 50 from base support 10. The spring 57 connected to each ball plunger is secured to a threaded stud 58 which is positioned in a threaded hole 59 in adaptor 50.

FIGS. 6-11 illustrate an alternate embodiment for adaptor 50 and planar reamer 30. In this alternate embodiment, the pivot mechanism between the adaptor 50 and planar reamer 30 includes a pivot pin 63 extending substantially perpendicularly from proximal adaptor surface 52 of adaptor 50. The supporting planar surface 32 of planar reamer 30 includes a corresponding pivot recess 43 for accepting pivot pin 63 of adaptor 50.

Figure 9:
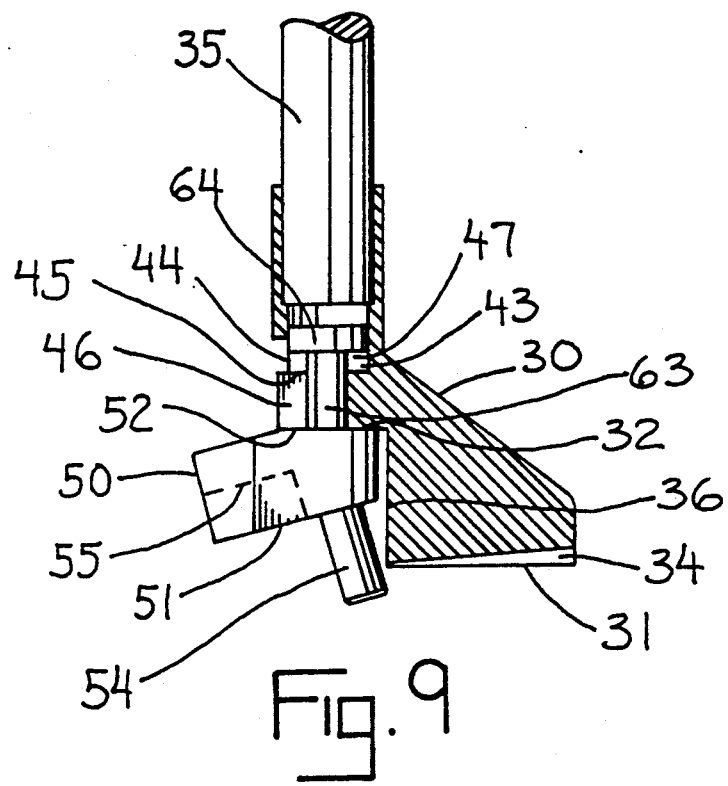
FIG. 9 is a side elevational view with the adaptor of FIG. 8 shown positioned in the planar reamer of FIG. 7 with the planar reamer shown in partial cross-section as in FIG. 7.
Figure 10:
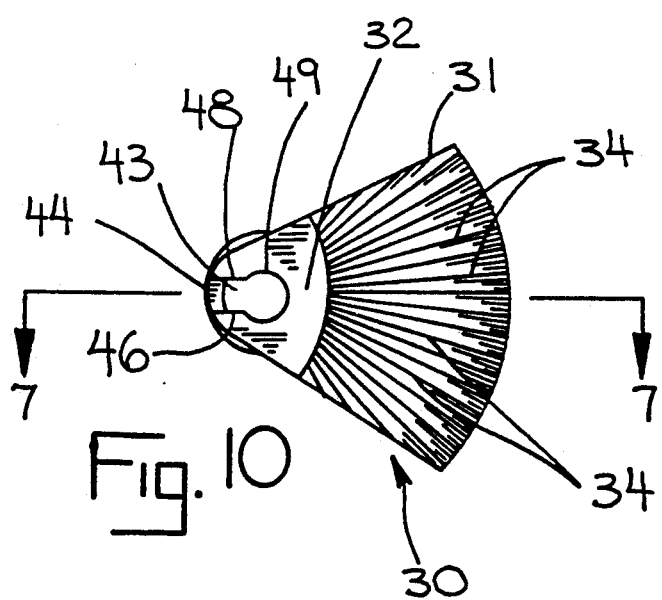
FIG. 10 is a bottom plan view of the planar reamer of FIG. 6.

The pivot recess 43 of planar reamer 30 includes a side opening 44 to allow the adaptor pivot pin 63 to pass through laterally into the pivot recess 43. The adaptor pivot pin 63 includes a post portion 65 with an enlarged circular head 64 thereon. The side opening 44 of pivot recess 43 extends into a slot 46 in a retaining platform 45. The side opening 44 also extends into an enlarged opening 47 above slot 46. Thus, the post portion 65 of pivot pin 63 can pass through the slot 46 in retaining platform 45, while the enlarged head 64 can pass through enlarged opening 47 above the retaining platform 45. The enlarged head 64 is larger than the slot 46 in the retaining platform 45, so that enlarged head 64 can not drop through the slot 46. Thus, the adaptor pivot pin 63 is retained longitudinally in the pivot recess 43, and requires lateral sliding of the pivot pin 63 through side opening 44 for insertion of pivot pin 63 into pivot recess 43 and for removal of pivot pin 63 from pivot recess 43. In addition, once enlarged head 64 is laterally inserted into opening 47, the pivot pin 63 can slide longitudinally upward within opening 47 as is illustrated in FIG. 9. Thus, pivot pin 63 may be prevented from laterally slipping out of opening 47 while supporting planar surface 32 and proximal adaptor surface 52 are in mating operative contact.

The slot 46 may suitably be keyhole-shaped having a narrow passageway 48 and an enlarged rounded end 49 at an end of the narrow passageway 48 oppositely located from the side opening 44. The post portion 65 of pivot pin 63 has a substantially circular cross-section with two oppositely located flats 66 thereon, as shown in FIG. 11. Thus, the narrow passageway 48 enables the post portion 65 of pivot pin 63 to pass through in a nonpivotal or nonrotatable orientation with flats 66 aligned with the passageway 48. The enlarged rounded end 49 of slot 46 enables the post portion 65 to pivot therein when the post portion 65 is located in end 49 of slot 46.

In accordance with the present invention, it is noted that the planar reamer 30 of the embodiments of FIGS. 1-5 or 6-11 could mate directly with a base support (not shown) without an adaptor therebetween by modifying the proximal planar surface of the base support to be at the same relative angle as the supporting planar surface of the planar reamer and by modifying the pivot mechanism at the proximal planar surface to mate with the perpendicular pivot orientation of the planar reamer, as appropriate. This would enable a planar surface to be cut by the depending cutting surface of the planar reamer at a level below the level of the mating pivoting surfaces of the proximal planar surface and mating supporting planar surface. It is noted that such a surgical reamer assembly provides an adjustment of the level of planar cutting, but does not adjust the angle of planar cutting. If an adjustment of the angle of the planar cutting is desired or an adjustment of the angle and the level of planar cutting is desired, an adaptor would also be used as described herein.

It is noted that the components of the surgical reamer assembly may be made from any appropriate materials suitable for surgical instruments. A particularly advantageous material for surgical bone cutting tools is stainless steel, although the material is not limited thereto. Any suitable manufacturing processes may be utilized to manufacture the components While this invention has been described in terms of particular advantageous embodiments, those skilled in the art can appreciate that modifications can be made without departing from the spirit and scope of this invention.

We claim:

1. A surgical reamer assembly for planing a bone surface comprising: a) a base support having a reference axis and a proximal planar surface oriented at a first angle to said reference axis; b) a planar reamer having a cutting surface oriented at a second angle to said reference axis, said second angle being different from said first angle, and a supporting planar surface connected to the cutting surface and also oriented at said second angle, and c) an adaptor for positioning between the base support and the planar reamer, the adaptor having a distal adaptor surface, oriented at said first angle for mating with and connecting to the proximal planar surface of the base support, and a proximal adaptor surface orientated at said second angle for mating with the supporting planar surface of the planar reamer, wherein the proximal adaptor surface and the mating supporting planar surface include a pivot means therebetween, thereby allowing pivoting of the planar reamer about said pivot means to provide planar reaming with said cutting surface.

2. The assembly of claim 1 wherein the pivot means includes a pivot pin extending substantially perpendicularly from the supporting planar surface of the planar reamer and the proximal adaptor surface includes a pivot recess for accepting the pivot pin of the planar reamer.

3. The assembly of claim 1 wherein the pivot means includes a pivot pin extending substantially perpendicularly from the proximal adaptor surface of the adaptor and the supporting planar surface of the planar reamer includes a pivot recess for accepting the pivot pin of the adaptor.

4. The assembly of claim 3 wherein the pivot recess in the planar reamer includes a side opening to allow the adaptor pivot pin to pass through laterally into the pivot recess.

5. The assembly of claim 1 wherein the pivot means includes a pivot pin extending perpendicularly from one of either the supporting planar surface of the planar reamer or from the proximal adaptor surface of the adaptor, and wherein the other of said two surfaces includes a pivot recess for accepting the pivot pin.

6. The assembly of claim 5 wherein the pivot recess includes a side opening to allow the pivot post to pass through laterally into the pivot recess.

7. The assembly of claim 6 wherein the pivot pin includes a post portion with an enlarged head on the post and wherein the side opening of the pivot recess opens into a slot in a retaining platform with an enlarged opening adjacent the slot, such that the post portion of the pivot pin can pass through the slot in the retaining platform and the enlarged head can pass through the enlarged opening adjacent the retaining platform, and wherein the enlarged head is larger than the slot in the retaining platform so that the enlarged head cannot pass longitudinally through the slot, thereby retaining the pivot pin longitudinally in the pivot recess, and requiring lateral sliding of the pivot pin through the side opening for insertion into and removal from the pivot recess.

8. The assembly of claim 1 wherein the cutting surface includes cutting teeth thereon.

9. The assembly of claim 1 wherein the planar reamer includes an elongated handle extending therefrom.

10. The assembly of claim 1 wherein the cutting surface depends from the supporting planar surface and is connected to the supporting planar surface by a connecting portion, such that the cutting surface is parallel to, but non-coplanar with the supporting planar surface.

11. The assembly of claim 10 wherein the base support includes an extending ledge surface about the base support spaced below said proximal planar surface, said ledge surface being oriented at said second angle, and wherein said cutting surface of the planar reamer is substantially coplanar with said ledge surface when the base support, adaptor, and planar reamer are assembled together.

12. The assembly of claim 11 wherein the base support includes a raised wall which separates the extending ledge surface from the proximal planar surface.

13. The assembly of claim 10 wherein the connecting portion is laterally spaced from the pivot pin.

14. The assembly of claim 10 wherein the cutting surface of the planar reamer is lower than the proximal planar surface of the base support when the reamer, the adaptor, and the base support are assembled together.

15. The assembly of claim 1 wherein the first angle is about 60 degrees and the second angle is about 45 degrees.

16. The assembly of claim 1 wherein an anti-rotation means is further provided between the adaptor and the base support.

17. The assembly of claim 1 wherein the adaptor is releasably connected to the base support and wherein the proximal planar surface of the base support includes a locating recess therein, and the adaptor includes a corresponding locating pin extending from the distal adaptor surface.

18. The assembly of claim 17 wherein an anti-rotation means is further provided between the adaptor and the base support.

19. The assembly of claim 18 wherein the anti-rotation means includes a raised spline extending from the proximal planar surface, said spline spaced from the locating recess, and wherein the distal adaptor surface includes a corresponding spline receptacle for receiving the spline.

20. The assembly of claim 19 wherein the spline includes a groove and the adaptor includes a ball plunger means which is biased to extend from the adaptor into the spline receptacle and into the groove of the spline when the adaptor is assembled to the base support to releasably retain the adaptor onto the base support.

21. The assembly of claim 20 wherein the ball plunger means is spring biased such that the ball plunger means compresses and recedes into the adaptor as the ball plunger means passes over the spline upon the application of connection force to connect the adaptor to the base support or upon application of separation force to remove the adaptor from the base support.

22. A surgical reamer assembly for planing a bone surface comprising: a) a base support having a reference axis and a proximal surface oriented at a first angle to said reference axis; b) a planar reamer having a cutting surface oriented at a second angle to said reference axis, said second angle being different from said first angle, and a supporting planar surface connected to the cutting surface and also oriented at said second angle, and c) an adaptor for positioning between the base support and the planar reamer, the adaptor having a distal adaptor surface, oriented at said first angle for mating with and connecting to the proximal planar surface of the base support, and a proximal adaptor surface oriented at said second angle for mating with the supporting planar surface of the planar reamer, wherein the proximal adaptor surface and the mating supporting planar surface include a pivot means therebetween, thereby allowing pivoting of the planar reamer about said pivot means to provide planar reaming with said cutting surface, and wherein the pivot means includes a pivot pin extending substantially perpendicularly from the proximal adaptor surface of the adaptor and the supporting planar surface of the planar reamer includes a pivot recess for accepting the pivot pin of the adaptor, and wherein the pivot recess in the planar reamer includes a side opening to allow the adaptor pivot pin to pass through laterally into the pivot recess, and wherein the adaptor pivot pin includes a post portion with an enlarged head on the post portion, and wherein the side opening of the pivot recess in the planar reamer extends into a slot in a retaining platform with an enlarged opening above the slot, such that the post portion of the adaptor pivot pin can pass through the slot in the retaining platform and the enlarged head can pass through the enlarged opening above the retaining platform, and wherein the enlarged head is larger than the slot in the retaining platform so that the enlarged head cannot drop through the slot, thereby retaining the adaptor pivot pin longitudinally in the pivot recess of the planar reamer, and requiring lateral sliding of the pivot pin through the side opening for insertion into and removal from the pivot recess.

23. The assembly of claim 22 wherein the slot is a keyhole shaped slot having a narrow passageway and an enlarged rounded end at an end of the narrow passageway oppositely located from the side opening, and wherein the post portion of the pivot pin has a substantially circular cross-section with two oppositely located flats thereon, so that said passageway enables the post portion of the pivot pin to pass through in a nonpivotal or nonrotatable orientation with the flats of the post portion aligned with the passageway and so that said enlarged rounded end of the slot enables the post portion to pivot therein.

24. A surgical reamer assembly for planing a bone surface comprising: a) a base support having a reference axis and a proximal planar surface oriented at a first angle to said reference axis; b) a planar reamer having a cutting surface oriented at a second angle to said reference axis, said second angle being different from said first angle, and a supporting planar surface connected to the cutting surface and also oriented at said second angle, said supporting planar surface including a pivot pin extending substantially perpendicularly therefrom; and c) an adaptor for positioning between the base support and the planar reamer, the adaptor having a distal adaptor surface, oriented at said first angle for mating with and connecting to the proximal planar surface of the base support, and a proximal adaptor surface orientated at said second angle for mating with the supporting planar surface of the planar reamer, wherein the proximal adaptor surface includes a pivot recess for accepting the pivot pin of the planar reamer, thereby allowing pivoting of the planar reamer about said pivot pin to provide planar reaming with said cutting surface.

25. A surgical reamer assembly for planing a bone surface comprising: a) a base support having a proximal planar surface; b) a planar reamer having a cutting surface connected to a supporting planar surface; and c) an adaptor for positioning between the base support and the planar reamer, the adaptor having a distal adaptor surface for mating with and connecting to the proximal planar surface of the base support, and a proximal adaptor surface for mating with the supporting planar surface of the planar reamer, wherein the proximal adaptor surface and the mating supporting planar surface include a pivot means therebetween, thereby allowing pivoting of the planar reamer about said pivot means to provide planar reaming with said cutting surface, and wherein the cutting surface depends from the supporting planar surface and is connected to the supporting planar surface by a connecting portion such that the cutting surface is lower than the proximal planar surface of the base support, when the reamer, the adaptor, and the base support are assembled together.

26. A surgical reamer assembly for planing a bone surface comprising: a) a base support having a proximal planar surface; and b) a planar reamer having a cutting surface connected to a supporting planar surface, said supporting planar surface adapted to mate with the proximal planar surface of the base support, and wherein the proximal planar surface and the mating supporting planar surface include a pivot means therebetween, thereby allowing pivoting of the planar reamer about said pivot mean to provide planar reaming with said cutting surface, and wherein the cutting surface depends from the supporting planar surface and is connected to the supporting planar surface by a connecting portion, such that the cutting surface is lower than the proximal planar surface of the base support, when the reamer is operatively assembled thereto.

* * * * *